United States Patent [19]

Wilmott et al.

[11] Patent Number: 5,010,110

[45] Date of Patent: Apr. 23, 1991

[54] WATER ACTIVATED SOLID EMOLIENT PRODUCT AND PREPARATION THEREOF

[75] Inventors: James M. Wilmott, Kinnelon; William H. Koelle, Morris Plains, both of N.J.; Alexander P. Znaiden, Sloatsburg, N.Y.

[73] Assignee: Avon Products, Inc., New York, N.Y.

[21] Appl. No.: 517,547

[22] Filed: Apr. 27, 1990

Related U.S. Application Data

[63] Continuation of Ser. No. 224,194, Jul. 21, 1988, abandoned, which is a continuation of Ser. No. 913,585, Sep. 30, 1986, abandoned, which is a continuation of Ser. No. 774,173, Sep. 9, 1985, abandoned, which is a continuation of Ser. No. 634,853, Jul. 26, 1985, abandoned.

[51] Int. Cl.$^5$ .................. A61K 47/00; A61K 7/025

[52] U.S. Cl. .................. 514/758; 424/64; 424/68; 424/DIG. 5; 514/846; 514/847; 514/873

[58] Field of Search .............. 514/758, 846, 847, 873; 424/64, 68, DIG. 5

[56] References Cited

U.S. PATENT DOCUMENTS

| | | | |
|---|---|---|---|
| 2,970,083 | 1/1961 | Boll | 424/DIG. 5 |
| 4,120,948 | 10/1978 | Shelton | 424/68 |
| 4,226,889 | 10/1980 | Yuhas | 424/DIG. 5 |
| 4,425,328 | 1/1984 | Nabial | 424/68 |

Primary Examiner—John W. Rollins

[57] ABSTRACT

A water activated solid, emollient preparation is disclosed, said preparation having a homogenous crystal/gel matrix which is capable of incorporating up to 30% by weight of emollient and holding it in a solid form. When the preparation is rubbed on wet skin, it deposits an elegant occlusive emollient film. A method of pouring and cooling said product into bars is also disclosed.

2 Claims, No Drawings

WATER ACTIVATED SOLID EMOLIENT PRODUCT AND PREPARATION THEREOF

This application is a continuaion of application Ser. No. 224,194, Jul. 21, 1988, now abandoned which is a continuation of application Ser. No. 913,585, filed Sep. 30, 1986, now abandoned, which is a continuation of application Ser. No. 06/774,173, filed Sep. 9, 1985, now abandoned, which is a continuation of application Ser. No. 06/634,853 filed Jul. 26, 1985, now abandoned.

The present invention relates to a solid emollient product which is activated by water and to the preparation thereof.

Emollients can be used to relieve dry skin or they can be applied merely because they are tactilly pleasurable. One of the major functions of most emollients is that they serve to replace or augment the natural surface lipids thus making the skin feel smoother by reducing surface friction. Other emollients work directly on the stratum corneum softening it while others, such as isopropyl myristate or palmitate, etc., soften the stratum corneum indirectly by preventing the loss of moisture through an occlusive barrier.

In the past, emollients have been typically applied in a solid, liquid, cream or gel base. The solid products have been either moisturizing soaps or "so-called" sticks (e.g., colognes, antiperspirants and deodorants). Neither of these forms delivers an adequate level of emollients to all skin areas. A more suitable product would be in the form of a conveniently-shaped bar which contains high levels of emollients and which, when rubbed on moist skin, deposits an occlusive film.

In view of the above, it is an object of the present invention to provide a solid bar whose emolliency and moisturization are activated by the interaction of the bar with water and to provide a method for preparing such a product. Another object is to provide a product which when rubbed on wet skin deposits an elegant, emollient and occlusive film which is left on the skin to produce a pleasant tactile perception and to improve the condition of the stratum corneum without causing irritation. Other objects and features will be in part apparent and in part pointed out hereinafter. The invention accordingly comprises the compositions and methods hereinafter described, the scope of the invention being indicated by the subjoined claims.

The composition of this invention comprises a mixture of stearyl alcohol and a metallic stearate such as sodium stearate in proportions sufficient to form a stable self-supporting solid product which is capable of incorporating up to about 30% by weight of an emollient. The use of sodium stearate and other mono, di or trivalent metal stearates such as zinc stearate and aluminum stearate to form emollient gels is well known in the cosmetic art as is the addition of emollients to stearyl alcohol based solids; however, the use of a combination of sodium stearate and stearyl alcohol creates a solid/gel matrix which enables the formulator to maintain optimal stability while incorporating unexpectedly high concentrations of liquid emollients into the bar. In general suitable products are obtained when the stearyl alcohol is present in an amount from about 45 to about 65% by weight and the sodium stearate is present in an amount from about 1 to about 12% by weight. Preferred compositions are obtained when the amount of stearyl alcohol is about 50 to 60% by weight, most preferably about 55%, and when the amount of sodium stearate is about 6 to 7% by weight.

The stearyl alcohol provides a crystal matrix which is strengthened by the presence of the sodium stearate gel resulting in a crystal/gel structure, which is stabilized by the addition of propylene glycol, water and alkyl esters as described below. The sodium stearate provides the principle lubricant when the product is exposed to water and allows it to glide over wet skin. In addition, it provides for the homogeneous mixing of the emollients in the water which permits them to be uniformly distributed over the entire skin surface. The nature and amount of the stearyl alcohol and sodium stearate are important to the provision of a cosmetically acceptable product. For example, if all other parameters remain constant, the appearance of the bar is dependent on the purity of the stearyl alcohol which, in general, should have a level of $C_{18}$ no less than 97.5% by weight to prevent the formation of large, unaesthetic white clusters of sodium stearate crystals throughout the bar.

The level and molecular weight distribution of the sodium stearate also has an effect on the product. For example, an insufficient level of sodium stearate will cause the bar to drag on the skin during application, whereas excessive levels of sodium stearate will lower the melting point of the product to an unsatisfactory level. The molecular weight distribution of the sodium stearate also has an effect on the product. While pure sodium stearate contains 100% $C_{18}$, the material which is commercially available contains a mixture of $C_{16}$, $C_{18}$, $C_{20}$ and other fatty acids. Of those materials which are commercially available, it is preferred to use one which has a lower molecular weight distribution such as from 45 to 60% by weight $C_{16}$ and 25 to 75% by weight $C_{18}$, more preferably from 50 to 57% $C_{16}$ and 38 to 46% $C_{18}$. One such suitable material is C1 sold by Witco Chemical.

The stability of the product is affected by the quantity of emollient present and, as above mentioned, up to 30% by weight of emollient can be included. Lower amounts, as for example, down to 1% can of course be used but such low levels produce little or no perceptible skin benefit while excess amounts will not be held within the solid/gel matrix of the bar and will result in syneresis at elevated temperatures. In view of these parameters, it is preferred that the emollient(s) be present in an amount between about 15 and 25%, most preferably in an amount of about 20% by weight based on the weight of the product.

Emollient blends may be used to achieve particular tactile properties not achievable with a single emollient. For example, one particularly desirable blend is provided by the combination of isopropyl palmitate, ethylhexyl palmitate, isopropyl isostearate, myristyl myristate and cetyl lactate but other blends may be devised depending on the properties sought. The emollient or blend of emollients can be selected from a wide variety of emollients including homo- or copolymers of dialkyl siloxane, polymers of propylene glycol, petroleum based hydrocarbon fluids or gels (e.g., mineral oil and petrolatum), animal or vegetable derived oils (e.g., lanolin and vegetable oil), propoxylated alkyl ethers and alkyl esters with alkyl esters being especially preferred. Typical alkyl esters include those of the formula:

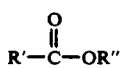

wherein R' and R" are alkyl groups having 2 to 24 carbon atoms, saturated or unsaturated, straight or branched chain. It is preferred that one or both R' and R" be derived from a fatty acid. Typical esters set forth by way of non-limiting example include isopropyl palmitate, ethylhexyl palmitate, isopropyl isostearate, myristyl myristate, cetyl lactate and the like.

In addition to the elegant tactile impression imparted to the skin with the use of emollients, those materials may serve as "crystallinity control agents." Particularly preferred is a combination of isopropyl palmitate and ethylhexyl palmitate in the ratio of 3 parts isopropyl palmitate to 1 part ethylhexyl palmitate. This mixture balances the hydrophilic/hydrophobic properties of the emollient phase so that it more uniformly interacts with the crystal/gel solid matrix. This produces a bar with a perceptibly homogeneous crystal structure throughout. The combination of isopropyl palmitate and ethylhexyl palmitate thus provides a product with good tactile performance and with an aesthetically pleasing homogenous appearance.

For a proper solubility balance so that the crystal/gel matrix forms homogenously and so that it is capable of holding the emollient phase, it is essential that a solubilizing agent such as an alcohol and/or water be present in an amount from about 2 to 12% by weight. Suitable alcohols contain 1 to 6 carbon atoms, straight or branched chain, including polyols such as propylene glycol. Particularly preferred is a combination of from about 2 to 10% by weight propylene glycol, most preferably about 6% by weight propylene glycol, and about 2 to 6% by weight water, most preferably about 3 to 4%. In this combination, the propylene glycol functions as a coupling and plasticizing agent. If insufficient quantities are used, then an irregular crystal structure will result which is manifested by the development of white sodium stearate crystals and a non-uniform, non-continuous surface on the finished product. An excessive amount of propylene glycol results in a depression in the melting point of the finished product to a temperature that is unsatisfactory for proper stability. The water is present as a solubilizing agent for the sodium stearate and at a level of 1 part water to 1.5-2.5 parts sodium stearate also increases the melting point of the product. If the water content is too low, then an irregular crystalline structure results which produces a discontinuous color distribution. Whereas, if too much water is incorporated into the base, the product will have a speckled appearance due to the accumulation of coloring materials in the pools of excess water.

Hydrogenated castor oil is preferably included for the purpose of controlling lathering of the product in the presence of water. It is important that the aqueous film deposited by the product not have a soapy appearance as the product is typically used immediately after the user has taken a shower or bath and before he or she has dried off. If the film looks soapy, the user will feel unclean. It has been found that an amount from about 1 to 10% by weight hydrogenated castor oil will control lathering, most preferably about 5% by weight. Levels much lower than 5% do not control the lather sufficiently, while no perceptible benefit is achieved by going to values greater than 8%.

Color agents can be added to the product to enhance its appearance. Of particular interest is the fact that the unique composition of the bar permits the use of either water or oil soluble dyes and pigment grinds in a suitable vehicle. Perfumes can be added to improve the consumer acceptability of the product. In addition, the perfume oil is generally miscible in the emollient phase. When the product is applied to wet skin the perfume is distributed over the body with the emollient(s) leaving a pleasant residual fragrance impression.

The product is made by heating the emollient or blend of emollients and the stearyl alcohol to about 190° F., with stirring until uniform. The sodium stearate is added and this mixture is held at 190° F. and stirred until the sodium stearate is uniformly dispersed. A premix is made of the solubilizing agents, such as water and propylene gylcol, in which the coloring material is typically dissolved. If pigment grinds or oil soluble dyes are used, these are added directly to the heated blend of emollients and stearyl alcohol. The premix is then added to the emollient(s)/stearyl alcohol/sodium stearate mixture, maintained at 190° F., and stirred until clear. The premix is cooled to 165° F., and a fragrance is added.

Once the mixture is made, the procedure for pouring the product into molds and cooling the resultant bars is critical for preparation of an acceptable product. It is also important that the product be cured for a number of days at ambient temperatures before it is used. In general, it is preferred that the product be poured at a temperature in the range of 160° to 165° F. If the product is poured at too high a temperature, i.e., above about 170° F., it will be insufficiently dense and an unacceptably large shrink hole will develop in the bar. On the other hand, if the product is poured at too low a temperature, i.e., below about 155° F., it will develop unattractive white crystalline surface clusters at the interface between the product and the mold.

In general, it is preferred that the bar be cooled in a cooling chamber or cooling tunnel at a temperature of about 40° F. or lower until the core temperature of the bar is less than about 95° F., otherwise surface blemishes will develop even though the mixture was poured at a suitable temperature. This is because there is a temperature gradient across the cooling bar. More particularly, when the surface temperature of the bar reaches 125° to 130° F., a solid product/mold interface is established. As the bar is further cooled, the crystal/gel matrix grows toward the interior of the bar. If the interior temperature of the bar is not reduced sufficiently before the bar is removed from the cooling chamber, the heat from the interior will be dissipated through the bar resulting in a disruption of the product surface with dimples or the like. When the cooling chamber is at 40° F. and the bars weigh about 85 to 95 g, it has been found sufficient to cool the product for about 40 minutes. The exact amount of time necessary to reduce the core temperature below about 95° F. for a particular bar will depend on a number of factors such as size and geometry of the bar, temperature of the cooling chamber, air flow over the product and so forth.

The cooled product is then preferably cured at a temperature preferably less than about 80° F. for about 7 days before it is used.

In use, the water activated solid, emollient preparation of the present invention is rubbed over the user's wet skin preferably just after the user has taken a shower or bath. As the product is rubbed over the user's wet skin, it delivers an emollient, occlusive film which is left on the skin to produce a pleasant tactile perception and to improve the condition of the stratum corneum.

The following example illustrates the invention, wherein percentages are by weight of the final product.

EXAMPLE 1

A conditioning body bar in accordance with the present invention was made up from the following ingredients:

| Ingredients | Percentage | Functionality |
| --- | --- | --- |
| Stearyl alcohol | 57.69 | Carrier |
| Isopropyl palmitate | 16.00 | Emollient, |
| Ethylhexyl palmitate | 5.00 | plasticizers |
| Hydrogenated castor oil | 5.00 | Lather control |
| Sodium stearate | 6.00 | Gellant, lubricant |
| Demineralized water | 3.00 | Solubilizers, |
| Propylene glycol | 6.00 | coupling agents |
| Color | 0.06 | |
| Fragrance | 1.25 | |

EXAMPLE 2

A conditioning body bar was made in accordance with Example 1 with stearyl alcohols of differing $C_{18}$ content:

| % $C_{18}$ | Observation |
| --- | --- |
| 98.5 | Uniform surface and interior. |
| 97.5 | Uniform surface and interior. |
| 96 | Random white crystal formation on surface and concentrated white clusters in the interior of the bar. |
| 93 | Pronounced white clusters on the surface and throughout the interior of the bar. |

EXAMPLE 3

A conditioning body bar was made in accordance with Example 1 at differing processing conditions:

| Pour Temp. | Cooling Time | Observation |
| --- | --- | --- |
| 165 | 40 min. | Large core hole formation |
| 160 | 40 min. | Acceptable |
| 160 | 35 min. | Slightly dimpled |
| 160 | 30 min. | Surface dimpling, fine white crystals at surface |
| 160 | 20 min. | Gross surface distortion |
| 160 | 50 min. | Acceptable |
| 155 | 40 min. | Slight dimpled surface |
| 150 | 40 min. | Grossly dimpled surface |

In view of the above, it will be seen that the several objects of the invention are achieved and other advantageous results attained. As various changes could be made in the above compositions and methods without departing from the scope of the invention, it is intended that all matters contained in the above description shall be interpreted as illustrative and not in a limiting sense.

What is claimed is:

1. The method of forming a stable, self supporting solid bar useful as a cosmetic comprising the steps of:
   (a) blending together the following ingredients at a temperature of about 190° F. to form a uniform liquid mixture with all percent weights being based upon the weight of the mixture unless otherwise indicated: about 45 to 65 percent by weight stearyl alcohol, said stearyl alcohol having a $C_{18}$ content of no less than about 97.5% by weight based upon the weight of the stearyl alcohol component, about 1-12 percent by weight sodium stearate, about 15-25 percent by weight emollient comprising one or more alkyl esters selected from the group consisting of isopropyl palmitate, ethyhexyl palmitate, isopropyl isostearate, myristyl myristate, and cetyl lactate, and a solubilizing agent of about 2-12 percent by weight, said solubilizing agent comprising a combination of about 2-6 percent by weight propylene glycol and about 2-6 percent by weight water,
   (b) allowing the mixture of step (a) to cool to a temperature in the range of about 160°-165° F.,
   (c) pouring the cooled mixture of step (b) into molds to form individual bars,
   (d) placing the molds in a cooling chamber maintained at a temperature of about 40° F. or less for a sufficient period of time until the interior temperature of the bars falls below about 95° F. without forming surface blemishes and,
   (e) curing the bars for at least 7 days at a temperature of 80° F. or less to form bars characterized by a homogeneous, single phase, crystal/gel structure throughout.

2. The product formed by the method of claim 1.

* * * * *